United States Patent

Kusumoto et al.

[11] Patent Number: 5,998,595
[45] Date of Patent: Dec. 7, 1999

[54] AZIDOHALOGENOBENZYL DERIVATIVES, SUGAR COMPOUNDS AND PROTECTION OF HYDROXY GROUPS

[75] Inventors: Shoichi Kusumoto, Minoh; Koichi Fukase, Kadoma, both of Japan

[73] Assignee: Wako Pure Chemical Industries, Ltd., Osaka, Japan

[21] Appl. No.: 08/961,174

[22] Filed: Oct. 30, 1997

[30] Foreign Application Priority Data

Nov. 5, 1996  [JP]  Japan ................................. 8-292955

[51] Int. Cl.⁶ ............................ C07H 1/00; C07C 247/16
[52] U.S. Cl. ................. 536/18.5; 536/18.6; 536/120; 552/1; 552/8; 570/182
[58] Field of Search ................. 536/18.5, 18.6, 536/120; 552/1, 8; 570/182

[56] References Cited

PUBLICATIONS

Wadzinsky et al. *J. Biol. Chem.*, vol. 262(36): 17683–17689, (1987). Abstracts only.
Golinsky et al. *Eicosanoids*, vol. 5(2): 87–97, (1992). Abstracts only.
Michalak et al. *J. Phys. Chem.*, vol. 100(33): 14028–14036, (1996). Abstracts only.
Egusa et al. *Synlett*, vol. 6, pp. 675–676, (1997). Abstracts only.

Fukase et al., "Application of 4–Azidobenzyl Group to Protection of Hydroxyl Functions", *Tetrahedron Letters*, 32, No. 29, 3557–3558, 1991.

*Primary Examiner*—Howard C. Lee
*Attorney, Agent, or Firm*—Leydig, Voit & Mayer, Ltd.

[57] ABSTRACT

Azidohalogenobenzyl derivatives of the formula (I)

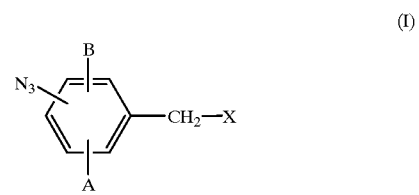

(I)

wherein A is a halogen atom, B is a halogen atom or a hydrogen atom, and X is a group reactive with a hydroxy group, methods of protecting hydroxy group(s) using said derivatives, and sugar compounds wherein a hydrogen atom of at least one hydroxy group is substituted by an azidohalogenobenzyl group. According to the present invention, there are provided novel derivatives capable of introducing a group into a compound having hydroxy group(s), which group is useful as a stable hydroxy-protecting group even in solid phase synthesis for the purpose of the extension of sugar chain under continuous acidic conditions and of being removed under mild conditions; sugar compounds protected by using said derivatives; and methods of protecting hydroxy group(s) using said derivatives.

10 Claims, No Drawings

AZIDOHALOGENOBENZYL DERIVATIVES, SUGAR COMPOUNDS AND PROTECTION OF HYDROXY GROUPS

TECHNICAL FIELD OF THE INVENTION

The present invention relates to novel azidohalogenobenzyl derivatives useful for protecting hydroxy group(s) of various compounds having hydroxy group(s), specifically sugars and sugar derivatives. More particularly, the present invention relates to novel azidohalogenobenzyl derivatives capable of introducing hydroxy-protecting group(s) which is(are) superior in resistance to acid and which can be removed under mild conditions. The present invention further relates to sugar compounds protected by using said derivatives and a method of protecting hydroxy group(s) using said derivatives.

BACKGROUND OF THE INVENTION

In a reaction using a compound having hydroxy group(s), particularly in the synthesis of sugar chain, sugar and its derivatives to be used for the reaction have many hydroxy groups which are undesirable in the formation of desired linkage. Therefore, it is required that such hydroxy groups be protected by protecting groups to prevent the participation in the reaction system for sugar chain extension. On the other hand, it is also necessary to successively eliminate protecting groups of certain hydroxy groups involved in the sugar chain linkage, so that they can function as acceptors. That is, in a sugar chain extension synthesis, for example, particular protecting groups are bound to specific hydroxy groups such that they can be removed where necessary, and a procedure of selective cleavage and linkage of new sugars to be added is repeated. These protecting groups are essentially required to allow selective elimination as necessary and to be stable under various conditions employed for the formation of glycoside linkage and cleavage of other protecting groups. In automatic synthesis such as solid phase synthesis, among others, the protecting group to be used needs to have superior resistance to acid, since Lewis acids are used for glycosidation, and the protecting group is continuously exposed to acidic environments.

In automatic synthesis of sugar chain, moreover, elimination of protecting groups needs to be done under relatively mild conditions of temperature and pH.

Conventional hydroxy-protecting groups, such as a p-methoxybenzyl group and a p-azidobenzyl group, permit elimination of protecting group under relatively mild conditions, and pose no problem in this regard. However, they are poor in resistance to acid, and efficient synthesis of sugar chain, particularly that of sugar chain having a side chain, using these protecting groups has been extremely difficult.

Despite various attempts so far made to develop a hydroxy-protecting group in view of such situation, a satisfactory hydroxy-protecting group has not been developed yet, which is superior in resistance to acid and which can be eliminated under mild conditions.

It is therefore an object of the present invention to provide novel derivatives capable of introducing hydroxy-protecting group(s) into compounds having hydroxy group(s), which can be used for conventional hydroxy group protection, conventional liquid phase synthesis of sugar chain and continuous sugar chain solid phase synthesis using automatic synthesis apparatuses.

It is also an object of the present invention to provide a sugar compound protected using said derivatives and a method for protection of hydroxy group(s) using said derivatives.

SUMMARY OF THE INVENTION

As a result of the study and investigation in an attempt to achieve the above-mentioned objects, it has been found that the hydroxy-protecting group obtained using the azidohalogenobenzyl derivatives of the formula (I) to be mentioned later has superior resistance to acid, can be quickly eliminated under mild conditions and is applicable to continuous sugar chain solid phase synthesis using automatic synthesis apparatuses.

Accordingly, the present invention provides the following.

(1) Azidohalogenobenzyl derivatives of the formula (I)

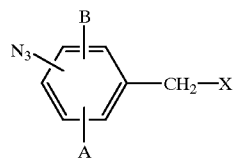

(I)

wherein A is a halogen atom, B is a halogen atom or a hydrogen atom, and X is a group reactive with a hydroxy group [hereinafter the derivative is to be referred to as azidohalogenobenzyl derivative (I)].

(2) The azidohalogenobenzyl derivatives according to (1) above, wherein X in the formula (I) is a halogen atom or an imidoyloxy group.

(3) The azidohalogenobenzyl derivatives according to (1) above, wherein, in the formula (I), B is a hydrogen atom and X is a halogen atom.

(4) The azidohalogenobenzyl derivative according to (1) above, which is 4-azido-3-chlorobenzyl bromide.

(5) Sugar compounds wherein a hydrogen atom of at least one hydroxy group is substituted by an azidohalogenobenzyl group of the formula (II)

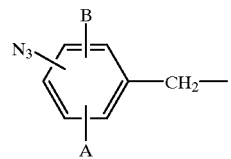

(II)

wherein each symbol is as defined above [hereinafter to be referred to as azidohalogenobenzyl group (II)].

(6) The sugar compounds according to (5) above, which are obtained by reacting a monosaccharide, an oligosaccharide or a polysaccharide with an azidohalogenobenzyl derivative (I).

(7) Methods of protecting hydroxy group(s), comprising reacting an azidohalogenobenzyl derivative (I) with a compound having hydroxy group(s) to substitute hydrogen atom(s) of hydroxy group(s) of said compound with an azidohalogenobenzyl group (II).

(8) The methods of (7) above, wherein the compound having hydroxy group(s) is a compound having a sugar structure.

(9) Reagents for protecting hydroxy group(s) comprising an azidohalogenobenzyl derivative (I).

(10) The reagents according to (9) above, wherein X in the formula (I) is a halogen atom or an imidoyloxy group.

(11) The reagents according to (9) above, wherein, in the formula (I), B is a hydrogen atom and X is a halogen atom.

(12) The reagents according to (9) above, wherein the azidohalogenobenzyl derivative is 4-azido-3-chlorobenzyl bromide.

DETAILED DESCRIPTION OF THE INVENTION

In the present invention, each substituent means the following.

A halogen atom includes a fluorine atom, a chlorine atom, a bromine atom and an iodine atom, preferably a chlorine atom and a bromine atom, and more preferably a chlorine atom.

The group reactive with a hydroxy group is one which reacts with a hydroxy group and can be eliminated along with a hydrogen atom of said hydroxy group. Examples thereof include the above-mentioned halogen atom, an imidoyloxy group and the like, preferably a halogen atom.

As used herein, an imidoyloxy group includes that having a $C_1$–$C_5$ alkyl group which may further have halogen atom(s) as substituent(s). Examples thereof include a 1,1,1-trichloroethanimidoyloxy group and the like.

The azidohalogenobenzyl derivatives (I) of the present invention are preferably exemplified by 4-azido-3-chlorobenzyl bromide and the like.

The azidohalogenobenzyl derivatives (I) of the present invention can be synthesized as in the following, when, for example, X is a halogen atom.

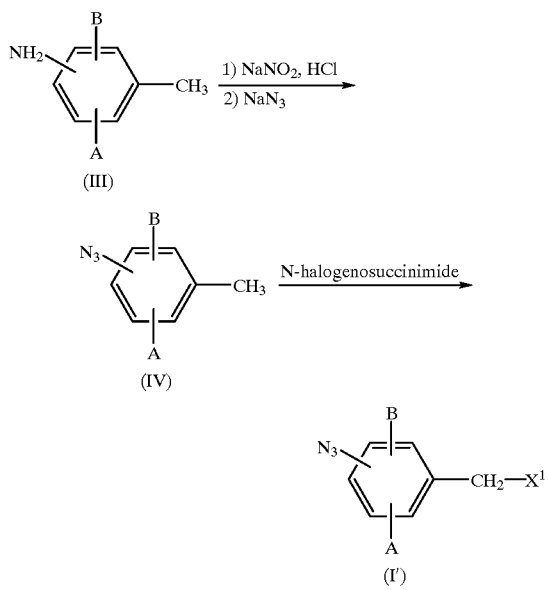

wherein X' is a halogen atom, and A and B are as defined above.

That is, aminohalogenotoluene of the formula (III) (hereinafter to be referred to as aminohalogenotoluene (III)) is treated with sodium nitrite in aqueous hydrochloric acid solution, and then with sodium azide to give azidohalogenotoluene of the formula (IV) (hereinafter to be referred to as azidohalogenotoluene (IV)) (Shinjikken Kagaku Koza XVI • Synthesis and Reaction of Organic Compounds III, Maruzen, Tokyo, Japan, pp. 1665–1666 (1978)). The resulting compound is, for example, reacted with N-halogenosuccinimide in the presence of a catalyst such as 2,2'-azobisisobutyronitrile (AIBN) in a suitable solvent, if necessary in an inert gas stream, in the shade to give azidohalogenobenzyl derivatives (I) of the present invention (Shinjikken Kagaku Koza XVI • Synthesis and Reaction of Organic Compounds I, Maruzen, Tokyo, Japan, pp. 336–339 (1979)).

A halogen gas, such as chlorine gas and bromine gas, a solid or liquid halogen, such as solid iodine and liquid bromine, may be used instead of N-halogenosuccinimide.

The azidohalogenotoluene (IV) is generally synthesized by adding sodium nitrite in an amount of 1 to 10 equivalents, preferably 1 to 5 equivalents, more preferably 1 to 2 equivalents to aminohalogenotoluene (III), stirring the resulting mixture at −10° C. to room temperature for several minutes to several dozen minutes, adding sodium azide in an amount of 1 to 5 equivalents, preferably 1 to 2 equivalents, to aminohalogenotoluene (III) and stirring the mixture at −10° C. to room temperature for several minutes to several dozen minutes.

Aminohalogenotoluene (III), the starting material, is exemplified by 2-amino-4-fluorotoluene, 2-amino-5-fluorotoluene, 2-amino-6-fluorotoluene, 3-amino-4-fluorotoluene, 3-amino-5-fluorotoluene, 3-amino-6-fluorotoluene, 4-amino-2-fluorotoluene, 4-amino-3-fluorotoluene, 2-amino-3-chlorotoluene, 2-amino-5-chlorotoluene, 2-amino-6-chlorotoluene, 3-amino-4-chlorotoluene, 3-amino-6-chlorotoluene, 4-amino-2-chlorotoluene, 4-amino-3-chlorotoluene, 2-amino-5-bromotoluene, 2-amino-6-bromotoluene, 2-amino-5-iodotoluene, 4-amino-2-iodotoluene, 4-amino-2,6-dichlorotoluene, 2-amino-4,6-dichlorotoluene, 4-amino-2,5-dichlorotoluene and the like.

In the reaction of azidohalogenotoluene (IV) with N-halogenosuccinimide, 1 to 5 equivalents, preferably 1 to 2 equivalents, of N-halogenosuccinimide is generally used relative to azidohalogenotoluene (IV). The solvents to be used for the reaction include, for example, aromatic hydrocarbon such as benzene, and halogenated hydrocarbon such as dichloromethane and dichloroethane. These solvents are preferably used in an anhydrous state. The reaction temperature is generally the boiling point of the solvent to be used and the reaction time is generally several dozen minutes to several dozen hours.

Examples of N-halogenosuccinimide to be used include N-chlorosuccinimide, N-bromosuccinimide, N-iodosuccinimide and the like.

When X is an imidoyloxy group, for example, a known synthetic method is used, such as a method wherein the corresponding azidohalogenobenzyl alcohol is reacted with trichloroacetonitrile in a solvent such as dichloromethane in the presence of sodium hydride (Jikken Kagaku Koza 4th ed., Organic Synthesis VIII, Maruzen, Tokyo, Japan, pp. 274–275 (1990)), or the corresponding azidohalogenobenzyl alcohol is reacted with trichloroacetonitrile in a solvent such as dichloromethane in the presence of caesium carbonate, to give azidohalogenobenzyl derivatives (I).

Thus obtained azidohalogenobenzyl derivative of the present invention is useful for protecting hydroxy group(s) of a compound having hydroxy group(s).

The compound having hydroxy group(s) includes a compound having a sugar structure.

By reacting the compound having a sugar structure with the azidohalogenobenzyl derivative(s) of the present invention, the sugar compound whose hydrogen atom(s) of the hydroxy group(s) is(are) substituted by the azidohalogenobenzyl group(s) is obtained.

The compound having a sugar structure includes monosaccharides (e.g., glucose, arabinose, fucose, galactose, mannose, xylose, fructose, lyxose, allose, arinose, ribose, talose, gulose, idose, altrose, sorbitol, mannitol, glucosamine and the like), oligosaccharides (e.g., maltose, isomaltose, turanose, gentiobiose, melibiose, planteobiose, primererose, vicianose, nigerose, laminaribiose, rutinose, cellobiose, xylobiose, maltotriose, gentianose, melezitose, planteose, ketose, trehalose, sucrose, lactose, raffinose, xylotriose and the like), polysaccharides (e.g., amylose, ficol, dextrin, starch, dextran, polydextrose, pullulan, cyclodextrin, glucomannoglycan, glucomannan, guar gum, gum arabic, glycosaminoglycan and the like), complex carbohydrates (e.g., glycopeptide, glycoprotein, glycolipid, proteoglycan and the like), and the like.

Those wherein a part of hydroxy group(s) in the compound having a sugar structure is(are) protected by, for example, an acyl group (e.g., an acetyl group, an acetylethylcarbonyl group and a benzoyl group), substituted alkyl (e.g., a benzyl group, a nitrobenzyl group, an azidobenzyl group and a methoxybenzyl group), and the like, are also included. Moreover, the compound having a sugar structure includes those linked to, for example, resin and polymer via a linker.

The sugar compound, wherein a hydrogen atom of at least one hydroxy group is substituted by an azidohalogenobenzyl group (II), can be obtained by reacting the above-mentioned compound having a sugar structure with azidohalogenobenzyl derivatives (I).

This reaction generally proceeds in a solvent such as N,N-dimethylformamide (DMF) at 0° C. to room temperature for several dozen minutes to several dozen hours. In this case, sodium hydride and the like are preferably used to activate a hydroxy group.

The sugar compound, wherein a hydrogen atom of at least one hydroxy group is substituted by an azidohalogenobenzyl group (II), is exemplified by methyl 6-O-(4-azido-3-chlorobenzyl)-2,3,4-tri-O-benzyl-D-glucopyranoside, methyl 4-O-(4-azido-3-chlorobenzyl)-2,3,6-tri-O-benzyl-D-glucopyranoside and the like.

The method of the present invention for protecting hydroxy group(s) comprises reacting an azidohalogenobenzyl derivative (I) with a compound having hydroxy group(s) to substitute hydrogen atom(s) of the hydroxy group(s) of said compound with azidohalogenobenzyl group (II).

The compound having hydroxy group(s) to be used in the present invention is preferably exemplified by the above-mentioned compounds having a sugar structure and sugar compounds wherein the oxygen atom of the ring forming the sugar structure of the compound having a sugar structure has been substituted by a sulfur atom or $CH_2$. However, said compound having hydroxy group(s) is not limited to those mentioned above, but may be any as long as it has hydroxy group(s).

The reaction of azidohalogenobenzyl derivative (I) with the compound having hydroxy group(s) is carried out according to the above-mentioned reaction of azidohalogenobenzyl derivative (I) with the compound having a sugar structure.

The compounds protected by the thus-obtained hydroxy-protecting group, namely, azidohalogenobenzyl group (II), can be easily deprotected under mild conditions according to the method described in, for example, Y. Oikawa et al., Tetrahedron Letters, 23, p. 885 (1982). To be specific, 1 to 5 equivalents, preferably 1 to 2 equivalents, of triphenylphosphine ($PPh_3$) to azidohalogenobenzyl group (II) is added and stirred, whereafter water, acetic acid and 1 to 5 equivalents, preferably 1 to 2 equivalents, of 2,3-dichloro-5,6-dicyanobenzoquinone (DDQ) to azidohalogenobenzyl group (II) are added and stirred to eliminate the protecting group with ease. Silica gel may be used instead of acetic acid.

The present invention is described in more detail by way of Examples, which should not be construed as limiting the invention. Production Example 1 : Synthesis of 4-azido-3-chlorotoluene. 4-Amino-3-chlorotoluene (14.16 g, 0.1 mol) was dissolved in a mixture of conc. hydrochloric acid (50 ml), water (400 ml) and DMF (100 ml), and was cooled with ice-brine. Thereto was added dropwise an aqueous solution (50 ml) of sodium nitrite (6.9 g, 0.1 mol) at −5° C. to 5C over 20 min. The resulting mixture was stirred for 10 min and an aqueous solution (50 ml) of sodium azide (6.5 g, 0.1 mol) was added dropwise at 10° C. to 20° C. over 20 min. The reaction mixture was stirred for 1.5 hr and extracted with diethyl ether (150 ml×3). The ether layers were combined and washed with saturated aqueous sodium hydrogencarbonate solution and saturated brine, and dried over anhydrous sodium sulfate. The solvent was evaporated under reduced pressure to give 17.14 g of the title compound as a brown oil. MS(EI): $M^+$=167, 16 g $^1$H-NMR (270 MHz, $CDCl_3$) δ: 7.19(d,1H), 7.06(m,2H), 2.31(s,3H)

EXAMPLE 1

Synthesis of 4-azido-3-chlorobenzyl bromide

4-Azido-3-chlorotoluene (17.14 g, 0.1 mol) was dissolved in dry benzene (80 ml) and thereto were added N-bromosuccinimide (19.6 g, 0.11 mol) and AIBN (1.64 g, 0.01 mol). The resulting mixture was refluxed in the shade in a nitrogen stream for 10 hr. Water (100 ml) was added and the mixture was filtrated. The aqueous layer of the filtrate was taken and extracted with ether. The organic layers were combined, washed with brine and dried over anhydrous sodium sulfate. The solvent was evaporated under reduced pressure and the obtained brown oil was purified by silica gel column chromatography (eluent; hexane) to give the title compound (14.2 g, yield 58%). m.p.: 75–77° C.

$^1$H-NMR (270 MHz, $CDCl_3$) δ: 7.42(d,1H), 7.31(dd,1H), 7.14(d,1H), 4.42(s,2H)

EXAMPLE 2

Synthesis of methyl 6-O-(4-azido-3-chlorobenzyl)-2,3,4-tri-O-benzyl-D-glucopyranoside Methyl 2,3,4-tri-O-benzyl-D-glucopyranoside (1.16 g, 2.5 mmol) was dissolved in DMF (10 ml) and thereto was added sodium hydride (60% in oil, 120 mg, 3.00 mmol) at 0° C., followed by stirring for 15 min. Then 4-azido-3-chlorobenzyl bromide (740 mg, 3.00 mmol) was added portionwise. The resulting mixture was stirred at 0° C. for 30 min and at room temperature for 3 hr. Ice-water was added and the mixture was extracted with ethyl acetate. The solvent was evaporated under reduced pressure and the residue was purified by silica gel column chromatography (eluent; hexane:ethyl acetate=4:1) to give the title compound as a yellow oil (1.48 g, yield 94%).

$^1$H-NMR (270 MHz, $CDCl_3$) δ: 7.37–7.03(m,18H), 5.00–4.35(m,9H), 3.98(t,1H), 3.76–3.52(m,5H), 3.38(s,3H)

EXAMPLE 3

Synthesis of methyl 4-O-(4-azido-3-chlorobenzyl)-2,3,6-tri-O-benzyl-D-glucopyranoside In the same manner as in Example 2, the title compound was obtained as a yellow oil (565 mg, yield 90%) by using methyl 2,3,6-tri-O-benzyl-D-glucopyranoside as the compound having a sugar structure.

$^1$H-NMR (270 MHz, CDCl$_3$) δ: 7.36–7.24(m,15H), 7.07 (d,1H), 6.97(m,2H), 4.98(d,1H), 4.80–4.62(m,6H), 4.43(d, 1H), 4.34(d,1H), 3.94(t,1H), 3.72–3.52(m,5H), 3.38(s,3H)

Experimental Example 1

Elimination of protecting group (synthesis of methyl 2,3,4-tri-O-benzyl-D-glucopyranoside).

Methyl 6-O-(4-azido-3-chlorobenzyl)-2,3,4-tri-O-benzyl-D-glucopyranoside (126 mg, 0.2 mmol) was dissolved in tetrahydrofuran (THF, 1 ml), and PPh$_3$ (63 mg, 0.24 mmol) was added thereto. The resulting mixture was stirred at room temperature for 1 hr. Then water (10 µl), glacial acetic acid (10 ml) and DDQ (68 mg, 0.3 mmol) were added and the reaction mixture was stirred for 1.5 hr. The reaction mixture was diluted with ethyl acetate, and washed with 5% aqueous ascorbic acid solution, saturated aqueous sodium hydrogencarbonate solution and saturated brine. After drying over anhydrous sodium sulfate, the solvent was evaporated under reduced pressure to give a brown oil. Purification thereof by silica gel column chromatography (eluent; dichloromethane:ethyl acetate=40:1) gave the title compound as a colorless oil (86 mg, yield 92%).

$^1$H-NMR (270 MHz, CDCl$_3$) δ: 7.37–7.24(m,15H), 4.99 (d,1H), 4.90–4.77(m,3H), 4.65(dd,2H), 4.58(d,1H), 4.00(t, 1H), 3.76–3.62(m,3H), 3.55–3.47(m,2H), 3.36(s,3H), 1.63 (t,1H)

Similar results were obtained by adding silica gel instead of acetic acid.

Experimental Example 2

Resistance to acid.

Methyl 6-O-(4-azido-3-chlorobenzyl)-2,3,4-tri-O-benzyl-D-glucopyranoside (compound of Example 2) was exposed to 2 equivalents of boron trifluoride-diethyl ether in methylene chloride at room temperature, but the compound was not decomposed.

Using [2-(4-methoxybenzyloxy)ethyl]benzene having a 4-methoxybenzyl group as a hydroxy-protecting group and methyl 6-O-(4-azidobenzyl)-2,3,4-tri-O-benzyl-D-glucopyranoside having a 4-azidobenzyl group as hydroxy-protecting group, similar experiment was performed. As a result, [2-(4-methoxybenzyloxy)ethyl]benzene was quickly decomposed and methyl 6-O-(4-azidobenzyl)-2,3,4-tri-O-benzyl-D-glucopyranoside was decomposed by about 25% in 6 hr.

From the foregoing, it is evident that, different from conventional hydroxy-protecting groups, the azidohalogenobenzyl group of the present invention shows superior stability to acid.

Experimental Example 3

Selective elimination.

(1) Synthesis of ethylene glycol protected by azidochlorobenzyl group and methoxybenzyl group: synthesis of 1-azido-2-chloro-4-(4-methoxybenzyloxyethoxymethyl) benzene.

2-(4-Methoxybenzyloxy)ethanol (500 mg, 2.75 mmol) was dissolved in DMF (10 ml), and sodium hydride (60% in oil, 132 mg, 3.30 mmol) was added at 0° C., which was followed by stirring for 30 min. Then 4-azido-3-chlorobenzyl bromide (813 mg, 3.30 mmol) was added portionwise. The resulting mixture was stirred at 0° C. for 30 min and at room temperature for 2 hr. Ice-water was added and the mixture was extracted with ether. The ether layer was washed with water and saturated brine, and dried over anhydrous sodium sulfate. The solvent was evaporated under reduced pressure and the residue was purified by silica gel column chromatography (eluent; hexane:ethyl acetate= 10:1) to give the title compound as a yellow oil (805 mg, yield 84%).

$^1$H-NMR (270 MHz, CDCl$_3$) δ: 7.39(d,1H), 7.30–7.24 (m,3H), 7.13(d,1H), 6.90–6.85(m,2H), 4.51(s,4H), 3.80(s, 3H), 3.64(s,4H)

(2) Elimination of azidochlorobenzyl group: synthesis of 2-(4-methoxybenzyloxy)ethanol.

1-Azido-2-chloro-4-(4-methoxybenzyloxyethoxymethyl) benzene (174 mg, 0.5 mmol) obtained in the above (1) was dissolved in THF (1 ml) and PPh$_3$ (157 mg, 0.6 mmol) was added thereto. The resulting mixture was stirred at room temperature for 1 hr. Then, water (10 ml), glacial acetic acid (10 ml) and DDQ (159 mg, 0.7 mmol) were added and the reaction mixture was stirred at room temperature for 1 hr. The reaction mixture was diluted with ethyl acetate and washed with 5% aqueous ascorbic acid solution, saturated aqueous sodium hydrogencarbonate solution and saturated brine. After drying over anhydrous sodium sulfate, the solvent was evaporated under reduced pressure to give a brown oil. Purification thereof by silica gel column chromatography (eluent; dichloromethane:ethyl acetate=2:1) gave the title compound as a yellow oil (68 mg, yield 75%).

$^1$H-NMR (270 MHz, CDCl$_3$) δ: 7.27(m,2H), 6.89(m,2H), 4.49(s,2H), 3.81(s,3H), 3.74(m,2H), 3.57(m,2H)

(3) Elimination of methoxybenzyl group: synthesis of 2-(4-azido-3-chlorobenzyloxy)ethanol.

1-Azido-2-chloro-4-(4-methoxybenzyloxyethoxymethyl) benzene (348 mg, 1 mmol) obtained in the above (1) was dissolved in THF (2 ml), and water (0.1 ml) and DDQ (34 mg, 1.50 mmol) were added. The resulting mixture was stirred at room temperature for 7 hr. Then, the reaction mixture was diluted with ethyl acetate, and washed with 5% aqueous ascorbic acid solution, saturated aqueous sodium hydrogencarbonate solution and saturated brine. After drying over anhydrous sodium sulfate, the solvent was evaporated under reduced pressure to give a brown oil. Purification thereof by silica gel column chromatography (eluent; hexane:ethyl acetate=2:1) gave the title compound as a yellow oil (201 mg, yield 88%).

$^1$H-NMR (270 MHz, CDCl$_3$) δ: 7.38(d,1H), 7.26(m,1H), 7.15(d,1H), 4.51(s,2H), 3.78(t,2H), 3.60(t,2H)

As described in the foregoing, the azidohalogenobenzyl group of the present invention can be deprotected under different conditions from those for conventional methoxybenzyl groups. To be specific, when using only DDQ and water, an azidohalogenobenzyl group is not deprotected, but methoxybenzyl group is deprotected, whereas using PPh$_3$, DDQ, water and acetic acid, azidohalogenobenzyl group is deprotected, but methoxybenzyl group is not deprotected. Thus, the azidohalogenobenzyl group of the present invention can be concurrently used with conventional protecting groups for selective elimination of protecting group.

The following Examples 4–9 show examples of synthesis of sugar chain by a solid phase synthesis method using the inventive protecting group, wherein the abbreviations in the reaction formulas mean the following.

Bzl: benzyl
Ph: phenyl
Trt: triphenylmethyl
MPM: 4-methoxybenzyl
Bz: benzoyl
Tce: 2,2,2-trichloroethyl
Troc: 2,2,2-trichloroethyloxycarbonyl
Et: ethyl
Bu: butyl
Tf: trifluoromethylsulfonyl
Ac: acetyl

EXAMPLE 4

Synthesis of phenyl 6-O-(4-azido-3-chlorobenzyl)-2,3,4-tri-O-benzyl-1-thio-D-glucopyranoside (4)

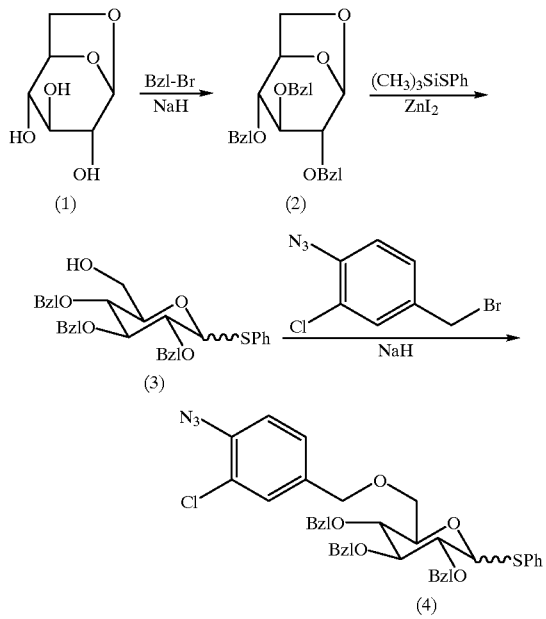

(a) 1,6-Anhydro-2,3,4-tri-O-benzyl-β-D-glucopyranoside (2)

Sodium hydride (60% in oil, 13.2 g, 0.33 mol) was washed with anhydrous ether, and suspended in DMF (100 ml). Thereto was added 1,6-anhydro-β-D-glucopyranoside (1) (16.2 g, 0.1 mol), and the resulting mixture was stirred at room temperature for 30 min. The reaction mixture was then cooled to 0° C. and benzyl bromide (39.3 ml, 0.33 mol) was added dropwise, which was followed by stirring at room temperature for 2 hr. Water (200 ml) was added and the mixture was extracted three times with ethyl acetate. The organic layers were combined, washed with saturated brine and dried over anhydrous sodium sulfate. The solvent was evaporated under reduced pressure to give white crystals. Recrystallization thereof from hot methanol gave 1,6-anhydro-2,3,4-tri-O-benzyl-β-D-glucopyranoside (2) (38.2 g, yield 88%) as white crystals.

(b) Phenyl 2,3,4-tri-O-benzyl-1-thio-D-glucopyranoside (3)

To a solution of 1,6-anhydro-2,3,4-tri-O-benzyl-β-D-glucopyranoside (2) (15.0 g, 34.7 mmol) and phenylthiotrimethylsilane (19.7 ml, 104 mmol) in dichloromethane (100 ml) was added zinc iodide (11.1 g, 34.7 mmol), and the resulting mixture was stirred at room temperature for 4 hr. The reaction mixture was filtrated, and the filtrate was concentrated under reduced pressure. The residue was dissolved in methanol (100 ml) and 1N hydrochloric acid (50 ml) was added, which was followed by stirring at room temperature for 15 min. Methanol was evaporated under reduced pressure and the residue was extracted with ethyl acetate. The organic layer was washed with saturated aqueous sodium hydrogencarbonate solution and saturated brine, and dried over anhydrous sodium sulfate. The solvent was evaporated under reduced pressure to give an oil which was crystallized from hexane to give phenyl 2,3,4-tri-O-benzyl-1-thio-D-glucopyranoside (3) as white crystals (19.5 g, yield 89%).

(c) Phenyl 6-O-(4-azido-3-chlorobenzyl)-2,3,4-tri-O-benzyl-1-thio-D-glucopyranoside (4)

To a solution of phenyl 2,3,4-tri-O-benzyl-1-thio-D-glucopyranoside (3) (1.09 g, 2.00 mmol) in DMF (10 ml) was added sodium hydride (60% in oil, 96 mg, 2.40 mmol), and the resulting mixture was stirred at room temperature for 15 min. The reaction mixture was cooled to 0° C. and 4-azido-3-chlorobenzyl bromide (592 mg, 2.40 mmol) was added, which was followed by stirring at room temperature for 4 hr. Water (30 ml) was added and the mixture was extracted twice with ethyl acetate. The organic layers were combined, washed with saturated brine and dried over anhydrous sodium sulfate. The solvent was evaporated under reduced pressure and the residue obtained was purified by silica gel column chromatography (eluent; hexane:ethyl acetate=5:1) to give phenyl 6-O-(4-azido-3-chlorobenzyl)-2,3,4-tri-O-benzyl-1-thio-D-glucopyranoside (4) (1.33 g, yield 94%) as slightly yellow crystals.

EXAMPLE 5

Synthesis of phenyl 6-O-(4-azido-3-chlorobenzyl)-2,3,4-tri-O-benzoyl-1-thio-β-D-glucopyranoside (11)

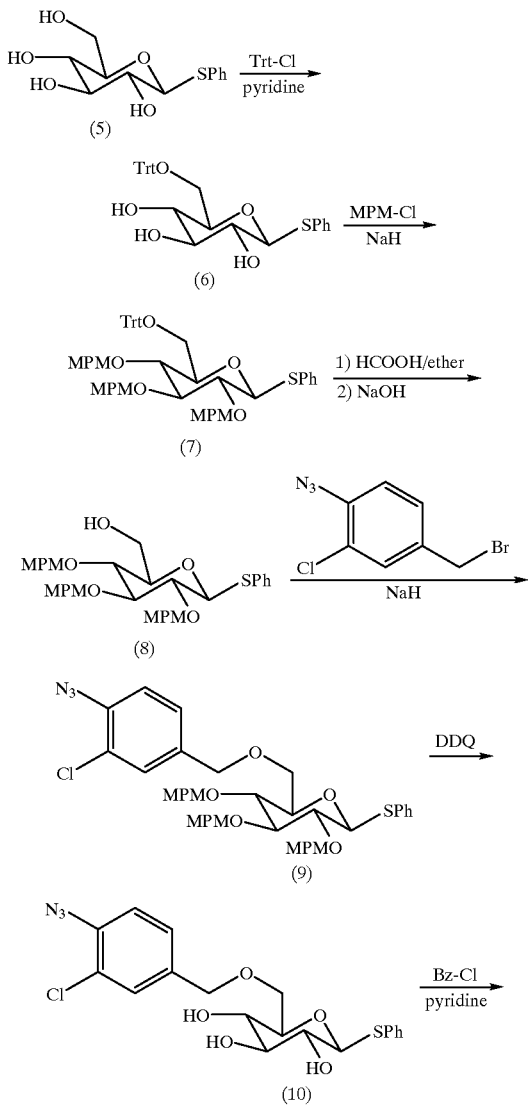

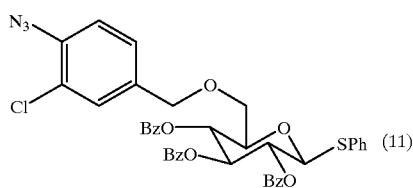

(a) Phenyl 6-O-triphenylmethyl-1-thio-β-D-glucopyranoside (6)

Phenyl 1-thio-β-D-glucopyranoside (5) (7.01 g, 25.8 mmol) and triphenylmethyl chloride (9.33 g, 33.5 mmol) were suspended in pyridine (20 ml), and the mixture was refluxed for 5 hr. The solvent was evaporated under reduced pressure and the residue was dissolved in ethyl acetate. The resulting solution was washed with water and saturated brine, and dried over anhydrous sodium sulfate. The solvent was evaporated under reduced pressure and the residue obtained was purified by silica gel column chromatography (eluent; dichloromethane:ethyl acetate=1:1) to give phenyl 6-O-triphenylmethyl-1-thio-β-D-glucopyranoside (6) (13.1 g, yield 99%) as a white solid.

(b) Phenyl 2,3,4-tri-O-(4-methoxybenzyl)-6-O-triphenylmethyl-1-thio-β-D-glucopyranoside (7)

Sodium hydride (60% in oil, 3.22 g, 80.5 mmol) was added to a solution of phenyl 6-O-triphenylmethyl-1-thio-β-D-glucopyranoside (6) (13.0 g, 25.3 mmol) in DMF (80 ml), and the resulting mixture was stirred at room temperature for 20 min. The reaction mixture was cooled to 0° C. and 4-methoxybenzyl chloride (12.6 g, 80.5 mmol) was added, which was followed by stirring overnight at room temperature. Cold water was added and the mixture was extracted twice with ether. The ether layers were combined and washed with water and saturated brine, and dried over anhydrous sodium sulfate. The solvent was evaporated under reduced pressure and the residue obtained was purified by silica gel column chromatography (eluent; hexane:ethyl acetate=3:1) to give phenyl 2,3,4-tri-O-(4-methoxybenzyl)-6-O-triphenylmethyl-1-thio-β-D-glucopyranoside (7) (18.8 g, yield 85%) as a white oil.

(c) Phenyl 2,3,4-tri-O-(4-methoxybenzyl)-1-thio-β-D-glucopyranoside (8)

To a solution of phenyl 2,3,4-tri-O-(4-methoxybenzyl)-6-O-triphenylmethyl-1-thio-β-D-glucopyranoside (7) (3.44 g, 3.93 mmol) in ether (8 ml) was added formic acid (8 ml), and the resulting mixture was stirred at room temperature for 5 hr. The reaction mixture was washed successively with water, saturated aqueous sodium hydrogen-carbonate solution and saturated brine, and the solvent was evaporated under reduced pressure. The residue was suspended in a mixture of ethanol (5 ml) and 1N aqueous sodium hydroxide solution (5 ml), and the suspension was stirred overnight at room temperature. Ethanol was evaporated under reduced pressure and the resulting suspension was extracted twice with ether. The combined ether layers were washed with saturated brine, and dried over anhydrous sodium sulfate. The solvent was evaporated under reduced pressure and the residue obtained was purified by silica gel column chromatography (eluent; hexane:ethyl acetate=2:1→1:1) to give phenyl 2,3,4-tri-O-(4-methoxybenzyl)-1-thio-β-D-glucopyranoside (8) (1.28 g, yield 51%) as white crystals.

(d) Phenyl 6-O-(4-azido-3-chlorobenzyl)-2,3,4-tri-O-(4-methoxybenzyl)-1-thio-β-D-glucopyranoside (9)

To a solution of phenyl 2,3,4-tri-O-(4-methoxybenzyl)-1-thio-β-D-glucopyranoside (8) (1.25 g, 1.98 mmol) and 4-azido-3-chlorobenzyl bromide (584 mg, 2.37 mmol) in DMF (10 ml) was added sodium hydride (60% in oil, 95 mg, 2.37 mmol), and the resulting mixture was stirred at room temperature for 3 hr. Cold water was added and the mixture was extracted twice with ether. The combined ether layers were washed with water and saturated brine and dried over anhydrous sodium sulfate. The solvent was evaporated under reduced pressure and the residue obtained was purified by silica gel column chromatography (eluent; hexane:ethyl acetate=4:1) to give phenyl 6-O-(4-azido-3-chlorobenzyl)-2,3,4-tri-O-(4-methoxybenzyl)-1-thio-β-D-glucopyranoside (9) as white crystals (1.25 g, yield 79%).

(e) Phenyl 6-O-(4-azido-3-chlorobenzyl)-1-thio-β-D-glucopyranoside (10)

To a solution of phenyl 6-O-(4-azido-3-chlorobenzyl)-2,3,4-tri-O-(4-methoxybenzyl)-1-thio-β-D-glucopyranoside (9) (1.24 g, 1.55 mmol) in dichloromethane (10 ml) were added water (0.5 ml) and DDQ (1.41 g, 6.21 mmol), and the resulting mixture was stirred at room temperature for 3 hr. Thereto was added 5% aqueous L-ascorbic acid solution, and the mixture was stirred for a while, and extracted with ethyl acetate. The organic layer was washed successively with saturated aqueous sodium hydrogencarbonate solution and saturated brine, and dried over anhydrous sodium sulfate. The solvent was evaporated under reduced pressure and the residue obtained was purified by silica gel column chromatography (eluent; dichloromethane:ethyl acetate=1:3) to give phenyl 6-O-(4-azido-3-chlorobenzyl)-1-thio-β-D-glucopyranoside (10) (584 mg, yield 86%) as yellow crystals.

(f) Phenyl 6-O-(4-azido-3-chlorobenzyl)-2,3,4-tri-O-benzoyl-1-thio-β-D-glucopyranoside (11)

To a solution of phenyl 6-O-(4-azido-3-chlorobenzyl)-1-thio-β-D-glucopyranoside (10) (580 mg, 1.32 mmol) in pyridine (5 ml) was added benzoyl chloride (609 μl, 5.28 mmol) at 0° C., and the resulting mixture was stirred at room temperature for 2 hr. Thereto was added water, and the mixture was extracted with ethyl acetate. The organic layer was washed with saturated brine, and dried over anhydrous sodium sulfate. The solvent was evaporated under reduced pressure to give phenyl 6-O-(4-azido-3-chlorobenzyl)-2,3,4-tri-O-benzoyl-1-thio-β-D-glucopyranoside (11) as slightly yellow crystals (934 mg, yield 94%).

EXAMPLE 6

Synthesis of polystyrene resin derivative of the formula (17) wherein 2,3,4-tri-O-benzyl-glucopyranoside is immobilized

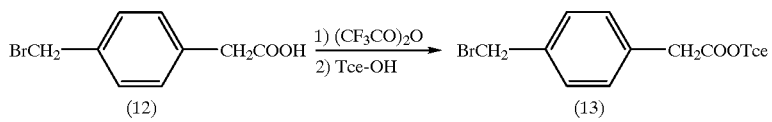

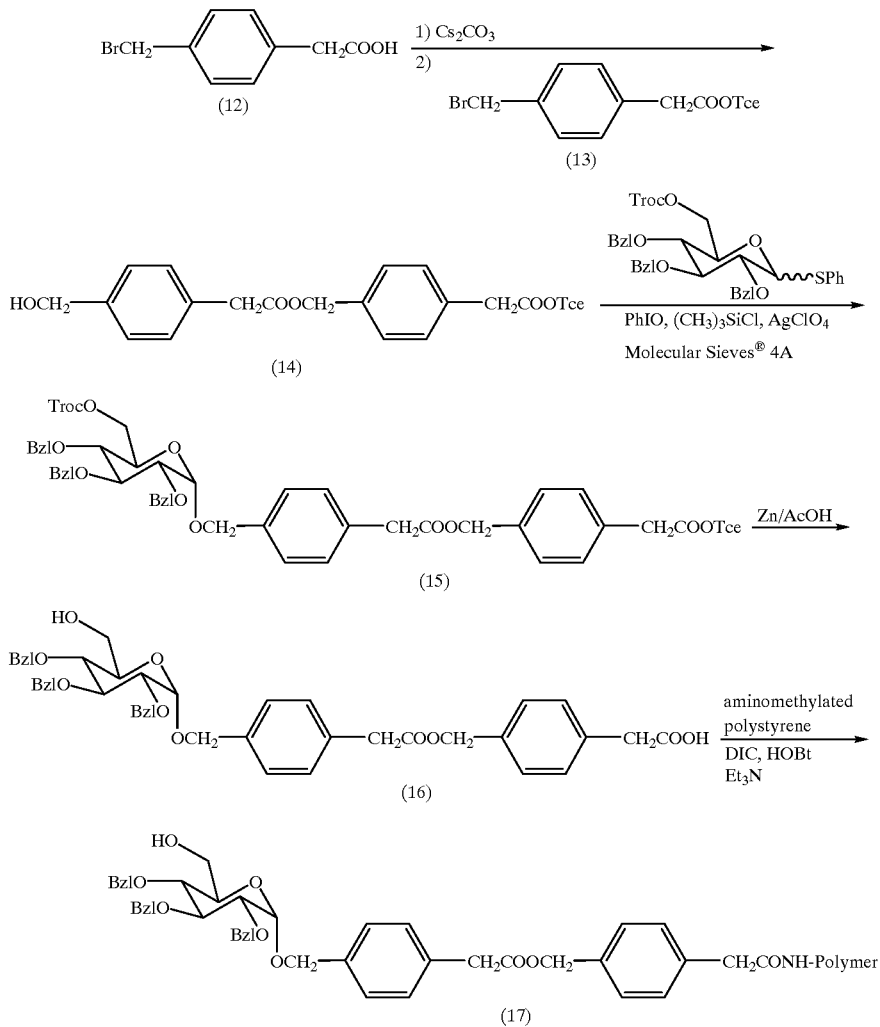

(a) 2,2,2-Trichloroethyl 4-bromomethylphenylacetate (13)

4-Bromomethylphenylacetic acid (12) (10.3 g, 44.8 mmol) was suspended in dichloromethane (30 ml). Trifluoroacetic anhydride (9.28 ml, 67.2 mmol) was added at 0° C., and the resulting mixture was stirred for 30 min. Then, 2,2,2-trichloroethanol (6.47 ml, 67.2 mmol) was added dropwise, and the resulting mixture was stirred at room temperature overnight. The reaction mixture was washed with water, saturated aqueous sodium hydrogencarbonate solution and saturated brine, and dried over anhydrous sodium sulfate. The solvent was evaporated under reduced pressure to give a colorless oil. The oil was left standing overnight to give 2,2,2-trichloroethyl 4-bromomethylphenylacetate (13) as white crystals (15.9 g, yield 98%).

(b) 2,2,2-Trichloroethyl 4-(4-hydroxymethylphenylacetoxymethyl)-phenylacetate (14)

To a solution of caesium carbonate (1.63 g, 5.00 mmol) in water (50 ml) was added 4-bromomethylphenylacetic acid (12) (1.15 g, 5.00 mmol), and the mixture was refluxed for one hour. After cooling, the reaction mixture was concentrated to dryness under reduced pressure. The residue obtained was suspended in DMF (10 ml). Thereto was added 2,2,2-trichloroethyl 4-bromomethylphenylacetate (13) (1.80 g, 5.00 mmol), and the resulting mixture was stirred at room temperature overnight. Water was added and the mixture was extracted with ethyl acetate. The organic layer was washed with saturated brine, and dried over anhydrous sodium sulfate. The solvent was evaporated under reduced pressure to give an oil which was purified by silica gel column chromatography (eluent; dichloromethane:ethyl acetate=15:1) to give 2,2,2-trichloroethyl 4-(4-hydroxymethylphenylacetoxymethyl)phenylacetate (14) as a white solid (994 mg, yield 45%).

(c) 2,2,2-Trichloroethyl ester derivative of the formula (15)

2,2,2-Trichloroethyl 4-(4-hydroxymethylphenylacetoxymethyl)-phenylacetate (14) (1.94 g, 4.35 mmol), phenyl 2,3,4-tri-O-benzyl-6-O-(2,2,2-trichloroethyloxycarbonyl)-1-thio-β-D-glucopyranoside (2.94 g, 3.95 mmol), iodosobenzene (956 mg, 4.35 mmol), silver perchlorate (328 mg, 1.58 mmol) and Molecular Sieves® 4A⁻ (ca. 1 g) were suspended in ether (15 ml), and the resulting suspension was stirred at room temperature for 30 min under a nitrogen atmosphere. The suspension was cooled to 0° C. and trimethylsilyl chloride (101 μl, 0.79 mmol) was added, which was followed by stirring for 30 min. The reaction mixture was filtered and the filtrate was washed with saturated aqueous sodium hydrogencarbonate solution and saturated brine, and dried over anhydrous sodium sulfate. The solvent was evaporated under reduced pressure and the residue obtained was purified by silica gel column chromatography (eluent; hexane:ethyl acetate=4:1) to give 2,2,2-trichloroethyl ester derivative of the formula (15) as a colorless oil (3.22 g, yield 77%). α-anomer/β-anomer=95/5

(d) Carboxylic acid derivative of the formula (16)

2,2,2-Trichloroethyl ester (15) (3.22 g, 3.06 mmol) was dissolved in 90% acetic acid, and zinc powder (4.00 g, 61.1 mmol) was added, which was followed by stirring at room temperature for 2 hr. The reaction mixture was filtrated and the filtrate was diluted with ethyl acetate, washed with saturated brine, and dried over anhydrous sodium sulfate. The solvent was evaporated under reduced pressure and the residue obtained was purified by silica gel column chromatography (eluent; dichloromethane:methanol=97:3) to give carboxylic acid derivative of the formula (16) as a white solid (2.11 g, yield 93%).

(e) Polystyrene resin derivative of the formula (17)

Carboxylic acid derivative of the formula (16) (896 mg, 1.20 mmol), aminomethylated polystyrene resin (0.83 mmol/g, 1.20 g, 1 mmol), diisopropylcarbodiimide (DIC) (219 μl, 1.40 mmol), 1-hydroxybenzotriazole (HOBt) (189 mg, 1.40 mmol) and triethylamine (195 μl, 1.40 mmol) were suspended in dichloromethane (10 ml), and the resulting suspension was shaken at room temperature for 2 hr. The resin was collected by filtration, washed with DMF and dichloromethane and dried under reduced pressure to give polystyrene resin derivative of the formula (17) (1.88 g, yield ca. 100%).

EXAMPLE 7

Glycosylation of polystyrene resin derivative of the formula (17) with 4-azido-3-chlorobenzylated thioglycoside of the formula (4) or the Formula (11)

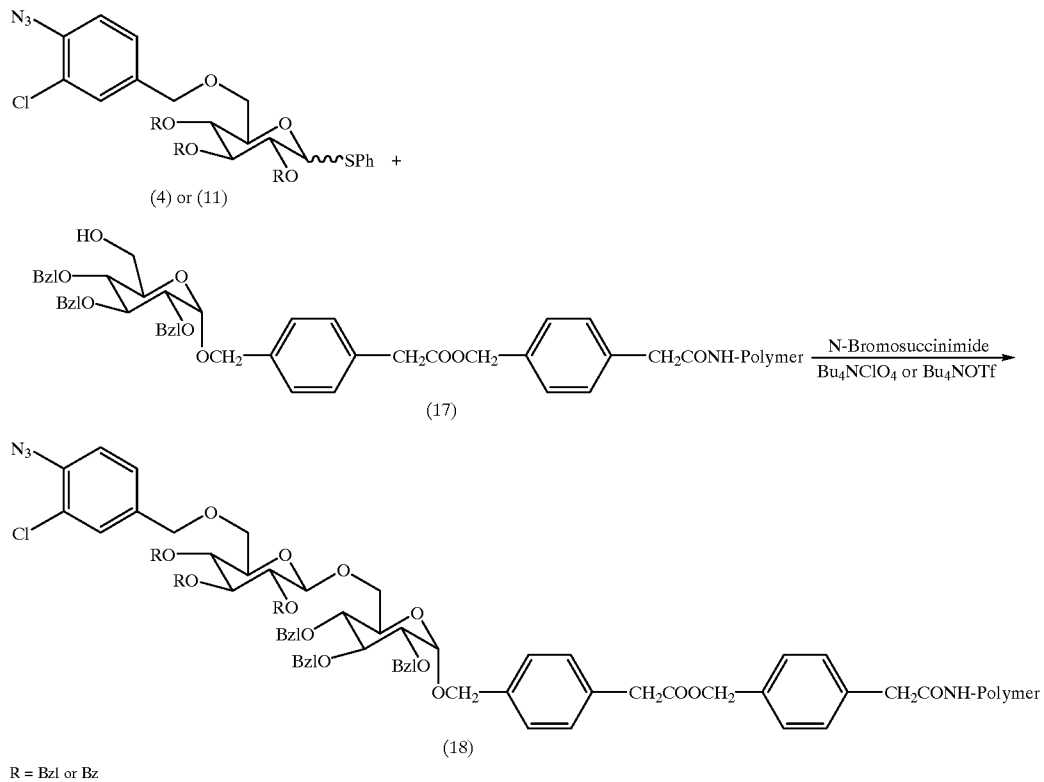

R = Bzl or Bz

Thioglycoside of the formula (4) (R=benzyl) or the formula (11) (R=benzoyl, 75 mmol) obtained in Example 4 or Example 5, polystyrene resin derivative of the formula (17) obtained in Example 6 (25 mmol), tetrabutylammonium salt (25 mmol) wherein when R=benzyl, tetrabutylammonium perchlorate was used and when R=benzoyl, tetrabutylammonium trifluoromethanesulfonate was used, and Molecular Sieves® 4A were suspended in dichloromethane (1 ml), and the resulting suspension was shaken for 15 min. Thereto was added N-bromosuccinimide (15 mg, 83 mmol), and the resulting mixture was mixed by shaking overnight. Molecular Sieves® 4A was removed and the resin was collected by filtration, washed with dichloromethane, and dried under reduced pressure to give polystyrene resin derivative of the formula (18). The introduction percentage of 4-azido-3-chlorobenzylated glycoside into the resin was 30–75%.

When the introduction percentage is poor, the reaction may be repeated 2 or 3 times.

EXAMPLE 8

Removal of 4-azido-3-chlorobenzyl group from polystyrene resin derivative of the formula (18)

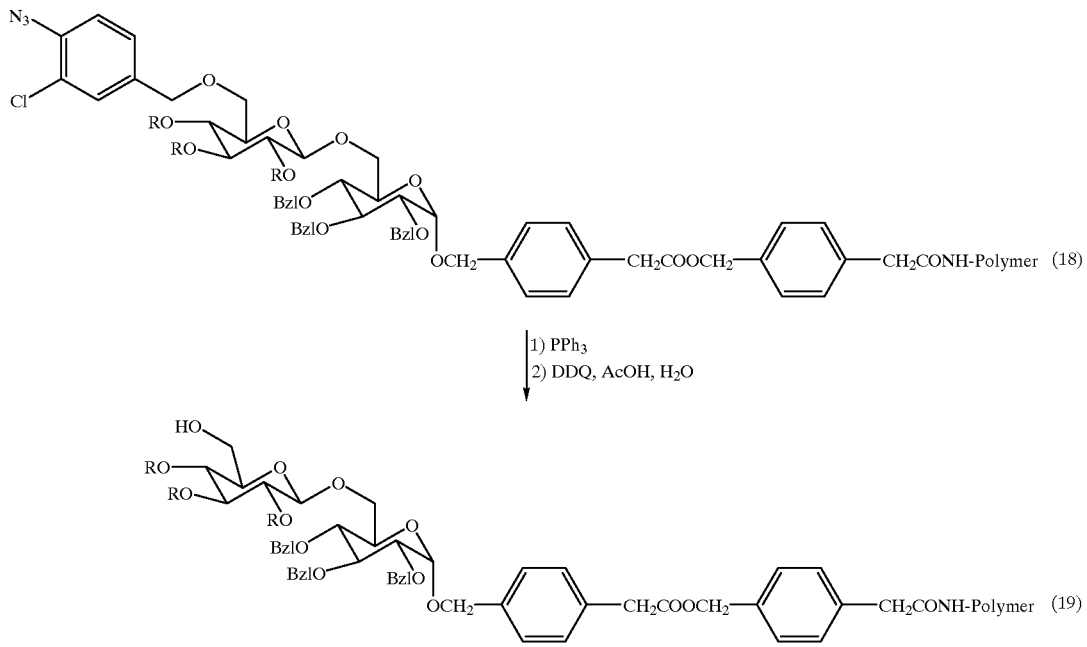

R = Bzl or Bz

Polystyrene resin derivative of the formula (18) having a hydroxy group protected by a 4-azido-3-chlorobenzyl group (ca. 70 mg, containing 10–15 μmol 4-azido-3-chlorobenzyl) and PPh$_3$ (20 mg, 75 μmol) were added to THF (1 ml), and the resulting mixture was shaken at room temperature for 1.5 hr. The resin was collected by filtration, washed with THF and added to THF (1 ml). Thereto were added DDQ (8.5 mg, 37.5 μmol) and 50% aqueous acetic acid solution (20 μl), and the resulting mixture was shaken at room temperature for 3 hr. The resin was collected by filtration, washed with DMF and dichloromethane and dried under reduced pressure to quantitatively afford polystyrene resin derivative of the formula (19).

EXAMPLE 9

Glycosylation of polystyrene resin Ddrivative of the formula (19) with 4-azido-3-chlorobenzylated thioglycoside of the formula (4) or the formula (11)

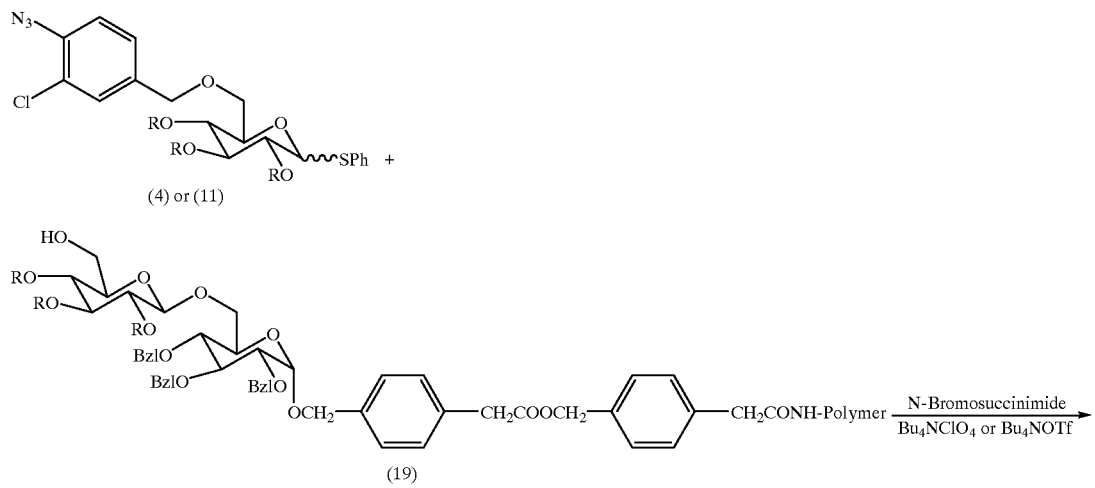

-continued

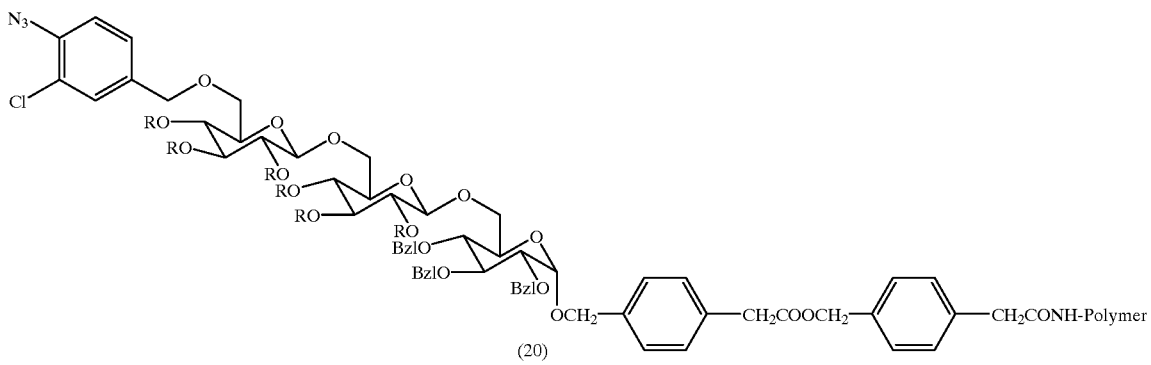

(20)

R = Bzl or Bz

Thioglycoside of the formula (4) (R=benzyl) or the formula (11) (R=benzoyl, 75 mmol), polystyrene resin derivative of the formula (19) (8 mmol), tetrabutylammonium salt (25 mmol) wherein when R=benzyl, tetrabutylammonium perchlorate was used and when R=benzoyl, tetrabutylammonium trifluoromethanesulfonate was used, and Molecular Sieves® 4A were suspended in dichloromethane (1 ml), and the resulting suspension was shaken for 15 min. Thereto was added N-bromosuccinimide (15 mg, 83 mmol), and the resulting mixture was mixed by shaking overnight. Molecular Sieves® 4A was removed and the resin was collected by filtration, washed with dichloromethane, and dried under reduced pressure to give polystyrene resin derivative of the formula (20). The introduction percentage of 4-azido-3-chlorobenzylated glycoside into the resin was 33%.

As mentioned above, the addition of an azido group to a benzyl group enables conversion thereof to an amino group where necessary by reduction. Consequently, protecting groups can be removed easily under mild conditions, wherein a halogeno group added to a benzyl group contributes to an improved resistance to acid. Therefore, the azidohalogenobenzyl group of the present invention is useful as a stable hydroxy-protecting group even in solid phase synthesis for the purpose of the extension of sugar chain under continuous acidic conditions. According to the present invention, there are provided azidohalogenobenzyl derivatives capable of introducing such azidohalogenobenzyl group, a sugar compound protected by using said derivatives, and a method of protecting hydroxy group(s) using said derivatives.

This application is based on application No. 292955/1996 filed in Japan, the content of which is incorporated hereinto by reference.

What is claimed is:

1. An azidohalogenobenzyl derivative of the formula (I)

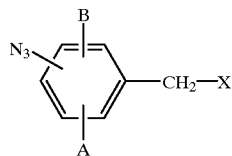

(I)

wherein A represents a single halogen atom, B represents a single halogen atom or a single hydrogen atom, and X is a halogen atom or an imidoyloxy group.

2. The azidohalogenobenzyl derivative according to claim 1, wherein, in the formula (I), B is a hydrogen atom and X is a halogen atom.

3. The azidohalogenobenzyl derivative according to claim 1, which is 4-azido-3-chlorobenzyl bromide.

4. A sugar compound wherein a hydrogen atom of at least one hydroxy group is substituted by an azidohalogenobenzyl group of the formula (II)

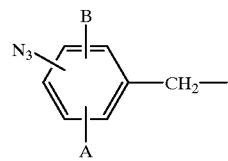

(II)

wherein A is a halogen atom, and B is a halogen atom or a hydrogen atom.

5. The sugar compound according to claim 4, which is obtained by reacting a monosaccharide, an oligosaccharide or a polysaccharide with an azidohalogenobenzyl derivative of the formula (I)

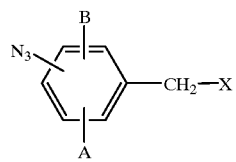

(I)

wherein A represents a single halogen atom, B represents a single halogen atom or a single hydrogen atom, and X is a halogen atom or an imidoyloxy group.

6. A method of protecting hydroxy group(s), comprising reacting an azidohalogenobenzyl derivative of the formula (I)

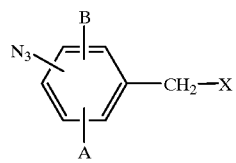

(I)

wherein A represents a single halogen atom, B represents a single halogen atom or a single hydrogen atom, and X is a halogen atom or an imidoyloxy group, with a compound having hydroxy group(s) to substitute hydrogen atom(s) of hydroxy group(s) of said compound with an azidohalogenobenzyl group of the formula (II)

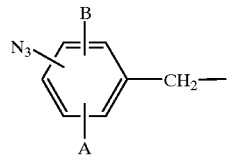
(II)

wherein A represents a single halogen atom, and B represents a single halogen atom or a single hydrogen atom.

7. The method according to claim 6, wherein the compound having hydroxy group(s) is a compound having a sugar structure.

8. A reagent for protecting hydroxy group(s) comprising an azidohalogenobenzyl derivative of the formula (I)

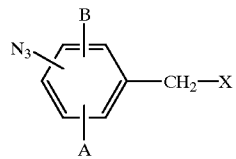
(I)

wherein A represents a single halogen atom, B represents a single halogen atom or a single hydrogen atom, and X is a halogen atom or an imidoyloxy group.

9. The reagent according to claim 8, wherein, in the formula (I), B is a hydrogen atom and X is a halogen atom.

10. The reagent according to claim 8, wherein the azidohalogenobenzyl derivative is 4-azido-3-chlorobenzyl bromide.

* * * * *